United States Patent [19]

Beer et al.

[11] Patent Number: 5,770,453

[45] Date of Patent: Jun. 23, 1998

[54] SENSORS FOR NEUTRAL MOLECULES

[75] Inventors: Paul Beer; Matthew Shade; Zheng Chen, all of Oxford, Great Britain

[73] Assignee: The Secretary of State for Defence in her Britannic Majesty's Government of the United Kingdom of Great Britain and Northern Ireland

[21] Appl. No.: 633,775

[22] PCT Filed: Oct. 18, 1994

[86] PCT No.: PCT/GB94/02276

§ 371 Date: Apr. 23, 1996

§ 102(e) Date: Apr. 23, 1996

[87] PCT Pub. No.: WO95/11449

PCT Pub. Date: Apr. 27, 1995

[30] Foreign Application Priority Data

Oct. 19, 1993 [GB] United Kingdom ................... 9321545

[51] Int. Cl.[6] ..................... G01N 27/333; G01N 33/00; C08K 5/15

[52] U.S. Cl. ..................... 436/149; 204/415; 422/82.01; 422/82.02; 422/82.03; 436/103; 436/104; 436/150; 436/151; 436/183; 524/108

[58] Field of Search ..................... 436/103–104, 436/149, 150, 151, 183; 422/81.01, 81.02, 81.03; 204/415; 524/108

[56] References Cited

U.S. PATENT DOCUMENTS

| 5,132,345 | 7/1992 | Harris et al. ............................. 524/108 |
| 5,216,185 | 6/1993 | Harris et al. ................................. 556/1 |

FOREIGN PATENT DOCUMENTS

| 0 490 631 A2 | 6/1992 | European Pat. Off. . |
| 2-15040 | 1/1990 | Japan . |
| WO 92/06128 | 4/1992 | WIPO . |

OTHER PUBLICATIONS

P.D. Beer et al. *J. Organomet. Chem.* 1988, 353, C10–C12.
P.D. Beer et al. *J. Organomet. Chem.* 1989, 378, 437–447.
A.M. Cadogan et al. *Analyst* 1989, 114, 1551–1554.
P.D. Beer et al. *J. Chem. Soc., Dalton Trans.* 1990, 3675–3682.
P.D. Beer et al. *J. Organomet. Chem.* 1991, 421, 265–273.
A.R. van Doorn et al. *J. Org. Chem,* 1991, 56, 2371–2380.
F. Porteu et al. *J. Phys. Chem.* 1991, 95, 7438–7447.
A. Cadogan et al. *Anal. Chem.* 1992, 64, 2496–2501.
P.D. Beer et al. *Tetrahedron* 1992, 48, 9917–9928.
P.D. Beer et al. *J. Chem. Soc. Chem. Commun.* 1993, 229–231.
P.R. Teasdale et al. *Analyst* 1993, 118, 329–334.
P.D. Beer et al. *J. Chem. Soc. Chem. Commun.* 1993, 828–830.
Atwood et al *Inorg. Chem.* 1992, 31, 603–606 "Metal Ion Complexes of Water–Soluble Calix[4]arenes".
Chemical Abstracts, vol. 118 (15), No. 146978b see compound RN146469–56–9.
Chemical Abstracts, vol. 117(21), No. 212471P see compounds RN 144151–17–7 and 117750–21–7.
Chemical Abstracts, vol. 107 (15), No. 134021u see compound RN 108817–14–7.

*Primary Examiner*—Arlen Soderquist
*Attorney, Agent, or Firm*—Nixon & Vanderhye

[57] ABSTRACT

A method for the detection of chemical agent present in a material comprising exposing a calixarene, having redox active substituents on its para rim, to a solution or suspension derived by admixture of all or some of the material with a liquid measuring any change in electrical behavior of the calixarene during or after exposure to the solution or suspension as compared to a reference condition, and relating such change in electrical behavior to the presence of chemical agent. Preferably, the calixarene exposed to the solution or suspension is a calix[4]arene or general formula (J), wherein $Y^1$ to $Y^4$ are independently selected from hydrogen, alkyl, alkenyl, aryl, aralkyl or a redox active substituent and $R^1$ to $R^4$ are independently selected from hydrogen, alkyl, alkenyl, aryl, aralkyl, or a polymerisable moiety, wherein at least one of $Y^1$ to $Y^4$ is a redox active substituent.

26 Claims, 10 Drawing Sheets

|−5μA

E/V vs. SCE

30 R = Ts
31 R = All

Fig. 12.

METAL-CONTROLLED SELECTIVE SUBSTITUTION

Mono-substitution

1,2-bis-substitution 1,3-bis-substitution

Tri-substitution

SENSORS FOR NEUTRAL MOLECULES

The present invention relates to the use of calixarenes in sensing chemical agents, particularly neutral charge agents, and to calixarene containing conductive materials sensitive to these agents. Further provided are electrodes incorporating these conductive materials, sensor devices incorporating such calixarene based electrodes and novel calixarenes suitable for use in such electrodes and devices.

A number of organic compounds have been demonstrated to have the ability to interact with neutral molecules in a host guest fashion whereby the neutral molecule is included within voids in the host compound. Examples of these interactions include those between cyclophanes and aromatics such as naphthalene, xylene and durene; between cryptophanes and chlorocarbons; and between cavitands and guests such as acetonitrile, chloroform and aromatics. These interactions have application in a variety of fields whereby a guest can be either applied in a solvent it is otherwise not soluble in, or in the removal or collection of the host from an environment where it in not desired or where it is to be recovered for use.

A further important group of host molecules are the calixarenes, a group of ring compounds comprising phenol formaldehyde condensation products, commonly having 4, 5, 6 or 8 phenolic monomers linked to each other at their 2, 5 positions; these particular molecules being referred to as calix[4]arenes, calix[5]arenes, calix[6]arenes and calix[8]arenes respectively. Study of complex formation of calixarenes with neutral molecules in chloroform utilising aromatic solvent-induced shift (ASIS) NMR has demonstrated a weak interaction between the tetrameric calix[4]arene and toluene guest on a 1:1 basis. Organic soluble calixarenes have failed to demonstrate complexation with numerous other guests, thought to be because of host solvent interaction (Gutsche and Bauer; Tet. Lett. (1981) 22 4763 and J.Am.Chem.Soc. (1985), 6052). The effects of dimethyl sulphide (DMS) on the cyclic voltammogram (CV) of bis(ferrocenoyl)-p-tert-butyl-calix[4]arene have been reported by J P Martin in his PhD thesis (October 1991- University of Birmingham, UK 'The synthesis and evaluation or calixarene hydrophobic hosts designed to recognise small organic molecules'). Upon addition of one equivalent or DMS current peak potentials were found to be shifted by 80 mV and −20 mV for oxidation and reduction respectively. Peak currents for both oxidation and reduction diminished by 15 to 20% simultaneously. This phenomenon was explained as being related to DMS inclusion at the 'upper rim' of the calixarene where para-substituents were present, whereby the substituents were pushed apart leading to conformational changes at the 'lower rim' giving rise to changes in the electronic environment. In this case the lower rim was substituted with a redox active substituent.

Although inclusion of the structurally similar DMSO has been demonstrated by crystal X-ray analysis, the inclusion of DMS as reported by Martin has proven difficult to reproduce. The failure to realise this effect has led the present inventors to reconsider the strategy of use of redox active calixarenes in sensing of neutral compounds, as they have determined that the distance between the 'upper rim' and 'lower rim' groups is too great for there to be a significant and reliable influence of lost guest interaction on the redox properties of the lower rim. They have instead provided a novel approach whereby they substitute calixarenes at the 'upper rim' with redox active groups and find that this gives reliable reporting of the presence of guest host interaction.

The present inventors have further found that the polymerisation of these calixarenes onto the surface of a conductive substrate does not produce a conductive effect whereby the upper rim conformational changes can be detected through that substrate. However, they have determined that if a copolymer of an organic conductive monomer and the calixarenes is so produced, these guest host conformational changes can be detected in this manner. Thus they have determined a method by which calixarene coated electrodes may be provided that can report back the presence of guest agents, particularly neutral molecules but also charged ones, to an electrical monitoring apparatus connected across a sampling cell.

A first aspect or the present invention provides a method for the detection or chemical agent present in a material comprising exposing a calixarene, having one or more redox active substituents on its para rim, to a solution or suspension of the material in a liquid, measuring any change in electrical behaviour of the calixarene during or after exposure to the solution or suspension as compared to a reference condition, and relating such change in electrical behaviour to the presence of chemical agent.

Preferably the calixarene exposed to the solution or suspension is a calix[4]arene or general Formula I wherein $Y^1$ to $Y^4$ are independently selected from hydrogen, alkyl, alkenyl, aryl, aralkyl or a redox active substituent and $R^1$ to $R^4$ are independently selected from hydrogen, alkyl, alkenyl, aryl, aralkyl, or a polymerisable moiety; wherein at least one of $Y^1$ to $Y^4$ is a redox active substituent.

Preferred polymerisable moieties are those having one or more polymerisable groups distal to the calixarene rings, particularly pyrrole or thiophene moieties or analogous 5, 6 or 7 membered rings capable of polymerisation with similar moieties to give a conductive polymer; such moieties preferably spacing the polymerisable group from the calixarene rings sufficiently to allow access to the upper rim by any chemical agent in suspension or solution, while allowing the 'tethering' of the rings to a substrate without sterically hindering the molecule such that a conductive surface cannot form.

Suitable groups $R^1$ to $R^4$ including polymerisable moieties have been found to include —$CH_2CONH(CH_2)_n$— $NC_4H_4$, where n is an integer which is preferably 2 to 4, most preferably 3, or its thiophene analogue, but may include polymerisable unsaturated moieties disclosed in EP0490631.

Suitable redox active substituents for $Y^1$ to $Y^4$ will be selected dependent upon the host molecule that is intended to be detected, but typically will be those including groups such as bis-(ferrocenoyl). imino dipyridyl and derivatives or complexes of these, or other such groups as act out in FIG. 1(a)–(d) below.

Preferred target agent guests for calixarenes using the method of the present invention are those that are potentially highly or super toxic agents likely to be present only in very small amounts in air or water, eg. chemical warfare agents such as sulphur or nitrogen mustard and their hemimustard derivatives (HMO), or toxics such as PCBs.

For the provision of substrates coated with calixarene moieties suitable for performance of host guest interaction measurements of the method of the present invention, there are provided novel polymers comprising the copolymerisation product of (a) calixarenes that have polymerisable moieties pendant from their lower rim, preferably from the oxygen atoms of their hydroxy subtituents and (b) one or more monomers polymerisable to electrically conductive polymers.

Preferably the molar ratio of (a) to (b) is approximately 1;1, but other ratios will be determinable as producing suitable conductive products by simple bench experimentation. Preferred monomers (b) are pyrrole and thiophene, although analogous 5, 6 and 7 membered ring compounds may be used.

The calixarene monomer (a) may be any such calixarene that has a guest host interaction induced change in electrical property that can be determined by monitoring an electrical property of its copolymer product with (b). Preferably the calixarene monomer is one of the compounds of Formula (I) above wherein at least one, preferably two, of the groups $R^1$ to $R^4$ are those having polymerisable moieties that can copolymerise with the monomer or monomers of (a). Examples of structures suitable for use in forming such a polymer are given in FIG. 2, it being understood by those skilled in the art that derivatives of these structures might also be used.

Preferably the copolymer is provided as a thin film upon the substrate, eg, on an electrode, by electropolymerisation from a suitable solvent. One preferred such method is to form a solution of equimolar amounts of the monomers (a) and (b) in an organic solvent, eg. acetonitrile; expose the surface of a substrate to be coated to this solution, and then to place an electrical potential across that substrate and a further substrate, eg. electrode, also exposed to the solution. Preferably potential cycling is carried out as is well known in the art (eg. Heinzi J. Topics in Current Chemistry, Streckhan ed. Springer-Verlag, Berlin Heidelberg, Vol. 152, p1 (1990). In this manner suitable calixarene bearing coated electrodes are provided that can be incorporated into sensor apparatus of the invention.

Further methods for applying calixarenes to surfaces such as to provide electrode capability are provided by incorporating them into a matrix of a coating material. One such matrix readily produced is that of polyvinylchloride which can be deposited onto a solid surface, eg. a glass rod, from a solution in a solvent such as dichloromethane with the calixarene. In order to provide conductance with the rod that is conveniently coated with a conductive coating such glassy carbon, indium-tin oxide or platinum, beforehand and for use a conductor is connected to an exposed surface of that coating.

Typical sensor apparatus of the invention incorporates at least one polymer or martix coated substrate of the invention, eg. as an electrode, and is structured such as to be capable of supporting a sample solution or suspension in contact with that such that electrical properties of the calixarene before and after exposure can be measured. In this manner presence of a target chemical agent will be determined if a predetermined electrical change occurs on exposure of the substrate to the solution or suspension.

It will be realised that the electrical property of the coated substrate may be determined in a number of optional ways, but one preferred such way is by use of cyclic voltammetry whereby a further electrode, connected to the substrate/ electrode via a circuit including a voltage source and measuring instruments, is exposed to the solution or suspension at the same time. The voltage across the substrate and further electrode is cycled and redox peaks in the current flow are monitored to determine changes in the calixarene on the substrate that are indicative of presence of target guest. A second method for determining the electrical properties of the coated substrate is by use of square wave voltammetry.

Alternatively the present invention provides a system which merely incorporates calixarenes of Formula I wherein $R^1$ to $R^4$ are of non-polymerisable type under cyclic voltammetry conditions, into the sample solution or suspension. This is then placed into a cyclic voltammetry device of conventional design whereby similar redox changes may be determined. Thus a sample to be tested merely is admixed with calixarene before processing in the voltammetry device. It would be expected that such system would probably not be as sensitive as the polymer coated electrode apparatus system unless some enhancement device was included that could amplify the signal provided by the change in calixarene property and pass the amplified signal to a display or audible warning device.

The present invention also provides novel calixarenes, polymers, and coated substrates for use in the method, systems and apparatus of the invention.

The calixarenes, polymers, coated substrates, method, systems and apparatus of the invention will now be exemplified by way of illustration only by reference to the following non-limiting embodiments set out in the Figures and Examples. Other embodiments falling within the scope of the invention will occur to those skilled in the art in the light of these.

BRIEF DESCRIPTION OF THE DRAWINGS

FIGS. 1(*a*) to 1(*d*) show the structure of redox centre containing substituents suitable for use as group $Y^1$ to $Y^4$ in some of preferred calixarenes of the invention.

FIGS. 5(*a*) and 5(*b*) show cyclic voltammograms for (i) the calix[4]arene used in Example 2 below in $CH_2Cl_2$ solution, (ii) with added DMS and (iii) with added DMSO.

EXAMPLE 1

Synthesis of Calix[4]arenes for use in the Method of the Present Invention

Para substituted calix[4]arenes were synthesised using standard synthetic methods similar to those described by J P Martin in his thesis of October 1991. University of Birmingham, UK. Formaldehyde in THF acetic acid was standard method of introduction of para-groups (see page 39 of the thesis).

Figure 7:
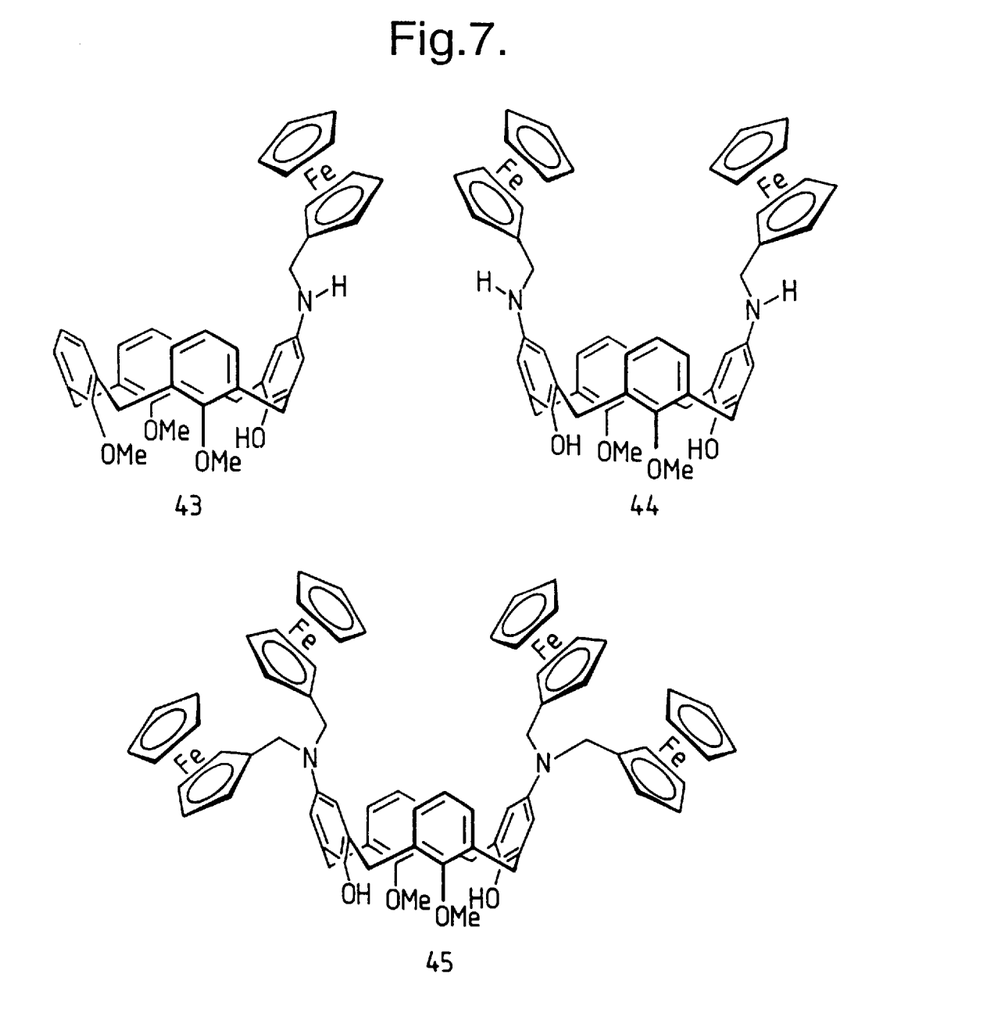
FIG. 7 shows the structure of compounds 43, 44 and 45 described in Example 1.
Figure 8:
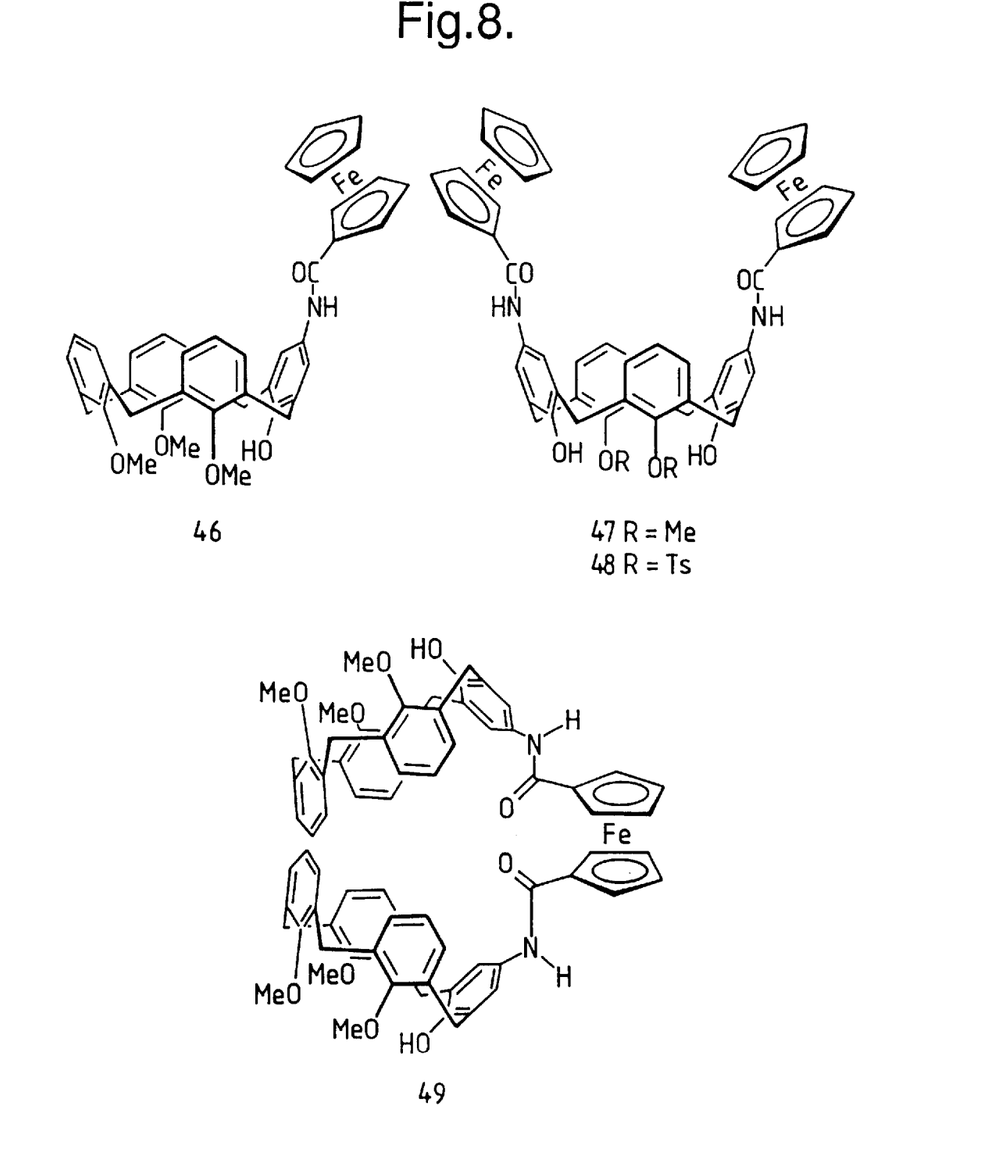
FIG. 8 shows the structure of compounds 46, 47, 48 and 49 described in Example 1.
Figure 9:
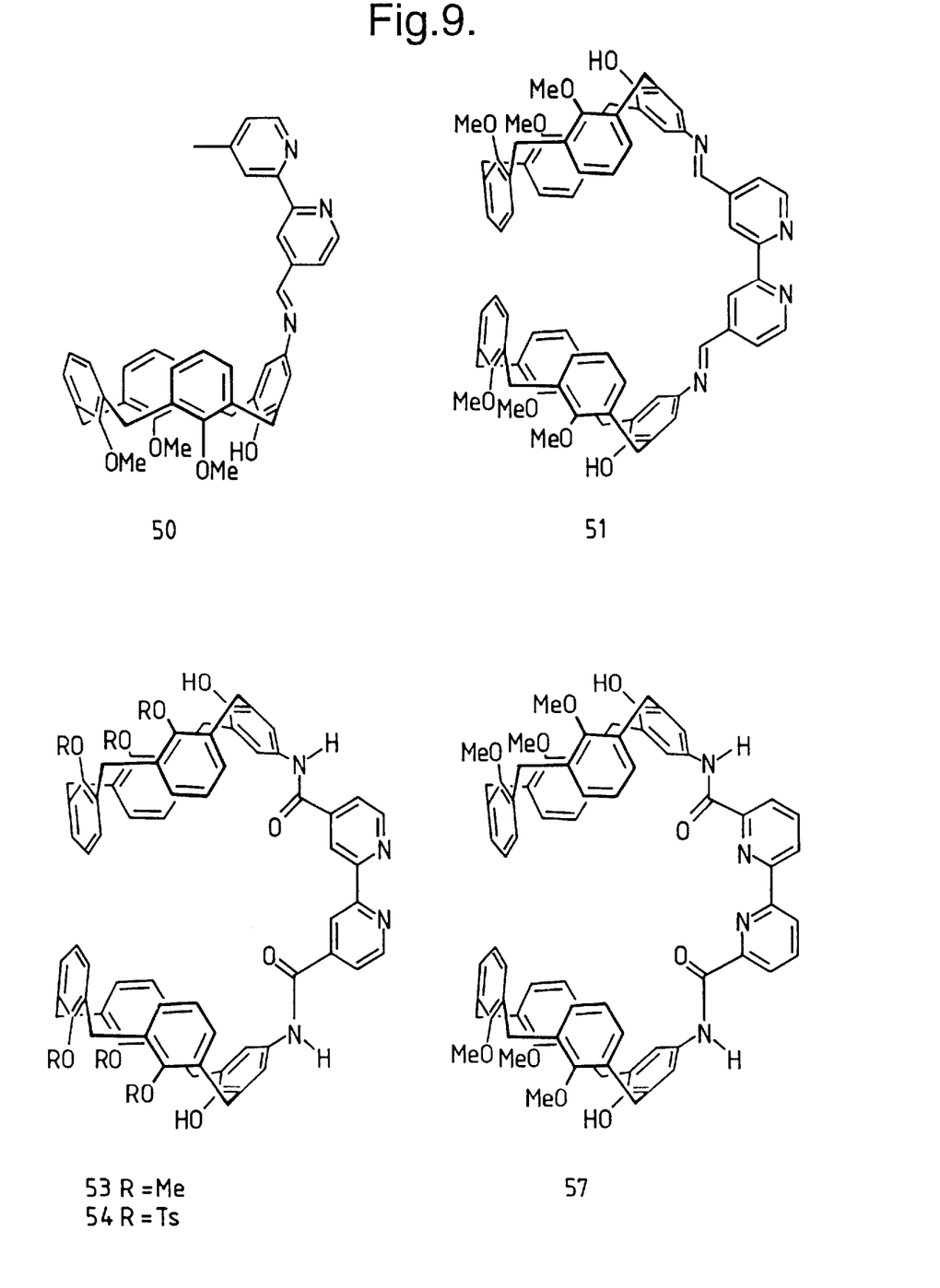
FIG. 9 shows the structure of compounds 50, 51, 52, 53, 54 and 57 described in Example 1.
Figure 10:
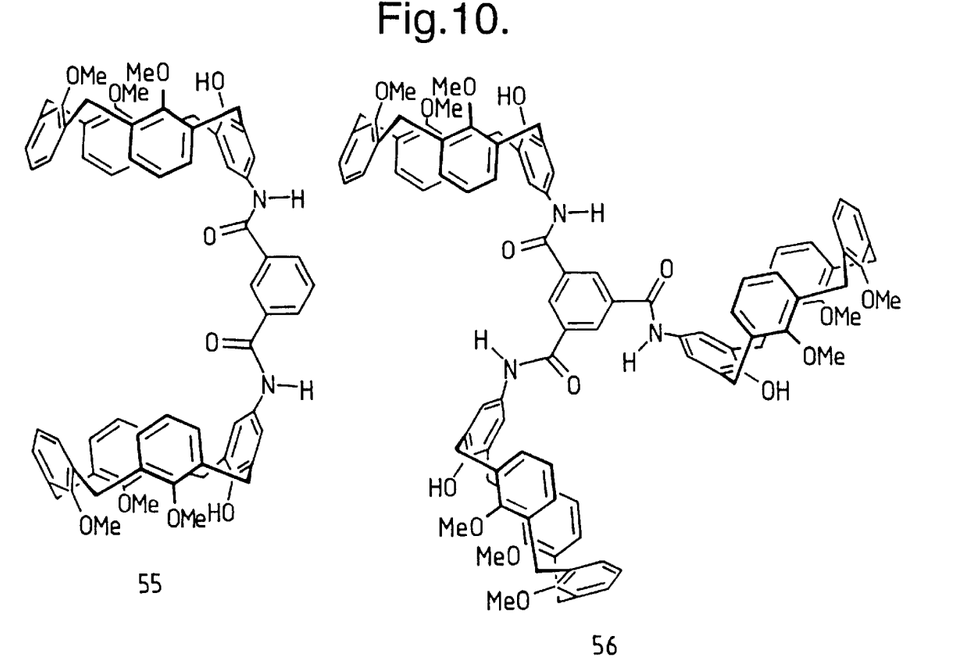
FIG. 10 shows the structure of compounds 55 and 56 described in Example 1.

Four types of calix[4]arenes were synthesised, (i) calix[4]arenes linked to ferrocenes by amine functional groups and containing a large cavity at the upper rim (compounds 43, 44 and 45 of FIG. 7), (ii) calix[4]arenes linked to ferrocenes by amide functional groups (compounds 46, 47, 48 and 49 of FIG. 8). (iii) calix[4]arenes linked to bipyridines by imine functional groups (compound 50 of FIG. 9), (iv) biscalix[4]arenes containing a number of spacer groups (compounds 50, 51, 53, 54, 55, 56, and 57 of FIGS. 9 and 10).

t-Butylcalix[4]arene (compound 1 of Table 1) was prepared on an 800 g scale and de-t-butylated by the method of Gutsche and Lin, Tetrahedron (1986) 42 p1633, with a number of 1,3-disubstituted calixarenes (3–18 of Table 1) being prepared from the product by refluxing it with $K_2CO_3$ (1.1 equivalents) and a respective alkylating agent (excess) in acetonitrile for 24 to 48 hours. Monomethylated calix[4]arene was prepared by the method of Reinhoudt, Tetrahedron (1991) 47, p8379, using $C_sCO_3$. Trimethylation of calix[4]arene 10 was achieved using BaO, $Ba(OH)_2$ as a base and dimethyl sulphate as alkylating agent in DMF by the method of Gutsche et al, Tetrahedron (1991) 39, p409.

Other trisubstituted calix[4]arenes were prepared by reacting 1,3-disubstituted calix[4]arenes with the required alkylating or tosylating reagent using NaH as base in THF; products 11, 13 and 15 being provided. $^1$II nmr spectra and X-ray crystallography were used to confirm product identity. A number of tetrasubstituted calix[4]arenes (12, 14, 16, 17, 18) were prepared by the reaction of a disubstituted calix[4]arene with NaH and excess alkylating or tosylating agent.

Figure 11:
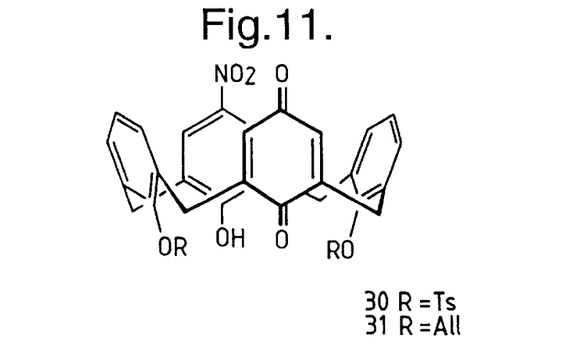
FIG. 11 outlines the synthesis of the structure of 58 and 59 and shows the structure of the nitro-quinone calix[4] arene.
Figure 12:
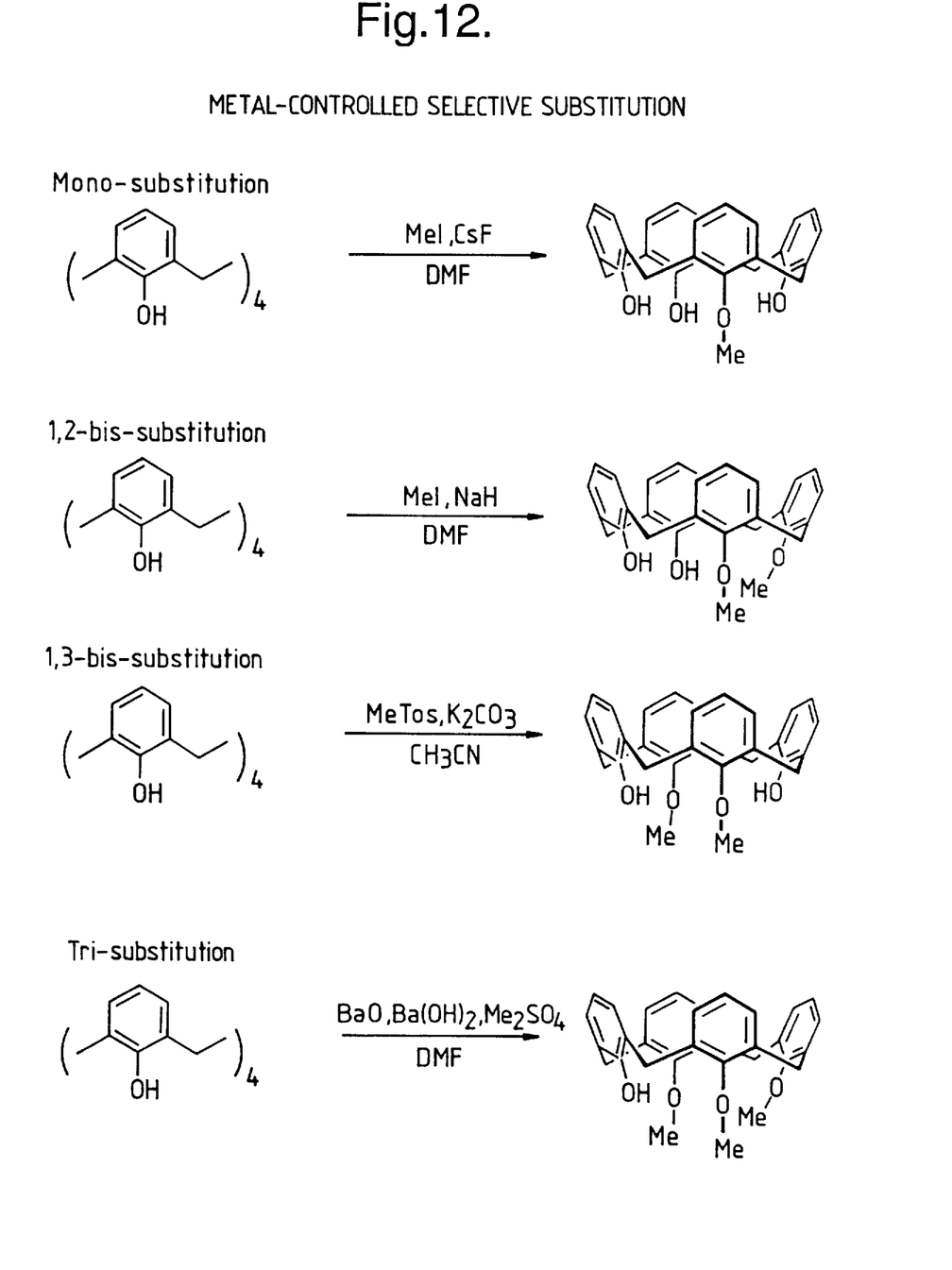
FIG. 12 outlines reaction schemes which may be used to provide specific substitution patterns on the lower rim; methylation is shown but replacement of Me by other required groups, eg. other alkyl groups, provides for their substitution.
Figure 13A:
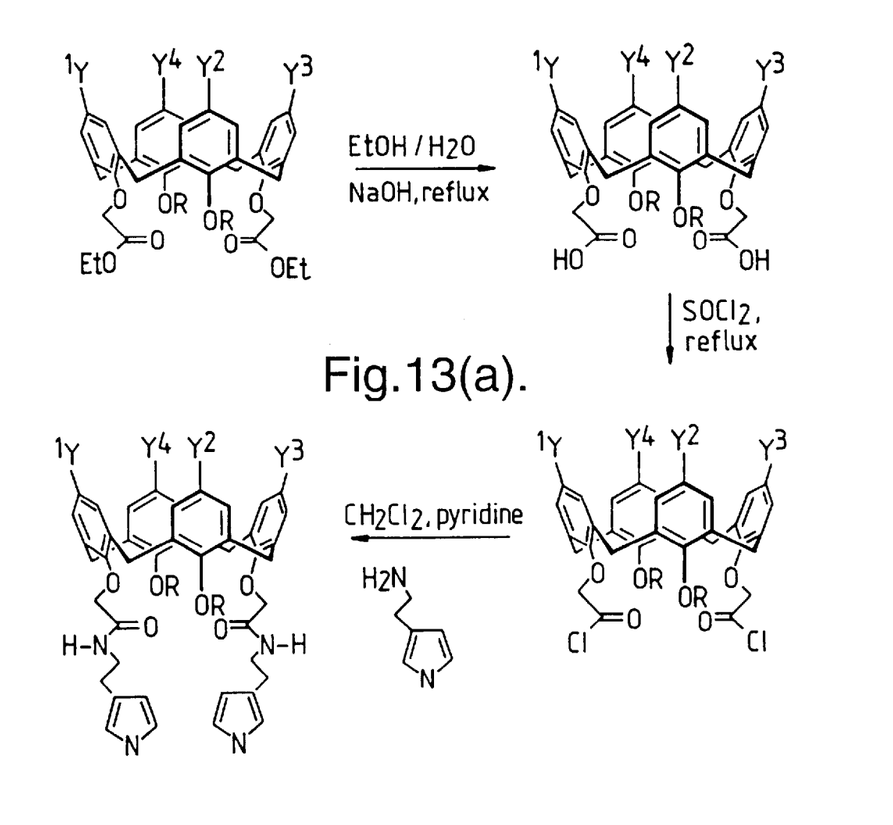
FIG. 13(a) outlines a reaction scheme for preparation of 3-substituted pyrrole ring containing calix[4]arenes.
Figure 13B:
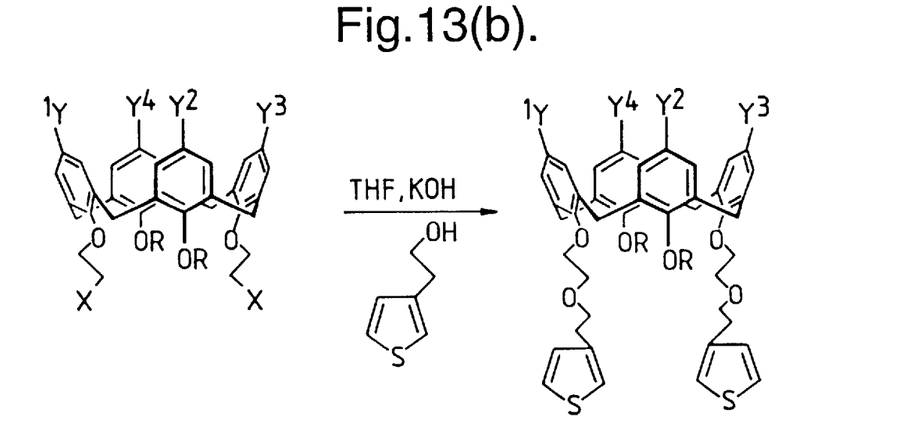
FIG. 13(b) outlines a reaction scheme for preparation of 3'-substituted thiophene ring containing calix[4]arenes.

The nitration of calix[4]arenes selectively substituted at the lower rim yields products which are nitrated at the positions para to the free phenols only. A method involving the nitration of the calix[4]arene with fuming nitric acid in a $CH_2Cl_2$/glacial acetic acid solvent system (Reinhoudt et al (1990) J. Org. Chem. 55, p5639) was used and found to give low and unpredictable yields. A new two phase nitration method was then found and developed and used for use with the calix[4]arenes (Keller (1994) Bull. Soc. Chim. Fr.131 p27); this allowing greater control over the distribution of products. Certain conditions allow the formation of nitroquinones 30 and 31 (see FIG. 14) rather than the nitrated calix[4]arenes 23 and 24, and also give higher yields of the nitrocalix[4]arenes 19, 23, 24, 27, 28 and 29.

A method for the nitrosation of the calix[4]arenes using amyl nitrate was developed showing the same selectivity as the nitrogen procedure and giving similar yields. As a method for the eletrophilic substitution of the calix[4]arenes it offers no advantage over the procedures for nitration, although different chemical properties of these novel nitroocalix[4]arenes 20, 21, 22 and 26 can be exploited to produce upper rim functionalized calix[4]arenes.

A number of other methods of introducing substituents were produced. The Claisen rearrangement of calix[4]arenes (Gutsche et al. J. Org. Chem. (1985) 50, p5802) bearing allyl functionalities on the lower rim (compounds 8 and 18) gave the upper rim substituted products 35 and 32. In one case the terminal alkene produced was isomerized to the internal alkene (Reinhoudt et al., J. Org. Chem. (1990) 55, p5639) (compound 33) which was then oxidised with $RuCl_3/NaIO_4$ to give carboxylic acid 34. Calix[4]arene was condensed with formaldehyde and dibenzylamine in a Mannich type reaction to give a new upper rim functionalized calix[4]arene 36 and applied to synthesis of ferrocene methylamine 59 via deprotection of dibenzylaminomethyl ferrocene 58.

Both nitro and nitrosocalix[4]arenes were reduced to amines by catalytic hydrogenation using Raney Nickel and hydrazine hydate. The calix[4]arene amines 39, 40, 41, 42 were condensed with a variety of redox active and spacer groups to give the final receptor molecules. All ferrocene and bipyridine compounds were characterised by $^1$H nmr and in some cases by FAB mass spectrometry and microanalysis.

Reaction of 41 and 42 with ferrocene carboxaldehyde gave the Schiff bases which were not isolated but reduced in situ to the amines 43 and 44; 44 then being further substituted to give compound 45. Reaction of 39 and 41 with ferrocene carbonylchloride gave compounds 46 and 47; compound 47 proving to be insoluble in dichloromethane and a number of other common organic solvents. To overcome problems associated with solubility a number of ferrocene derivatized calix[4]arenes with more lipophilic t-butyl and ethyl esters on the lower rim were prepared which also proved to be relatively insoluble in a range of organic solvents. Tosylated compound 48 was prepared from compound 40 and showed a much greater solubility in chlorinated organic solvents than 47. The condensation of 41 with 4-carboxaldehyde-4'-methylbipyridine gave Schiff-base product 50.

A number of biscalix[4]arenes 49, 51, 53, 54, 55 and 56 were prepared by the condensation of the calix[4]arene monoamines 41 and 42 with disubstituted redox-active and spacer groups. A triscalix[4]arene 57 was also prepared. Attempts to complex 53 with $Ru(bipyridyl)_2Cl_2.2H_2O$ proved unsuccessful and more soluble analogue 54 was synthesized.

EXAMPLE 2

Effect of Guest Host Interaction upon Cyclic Voltammagram of Calix[4]arenes in Solution in Method of Invention.

Figure 4:
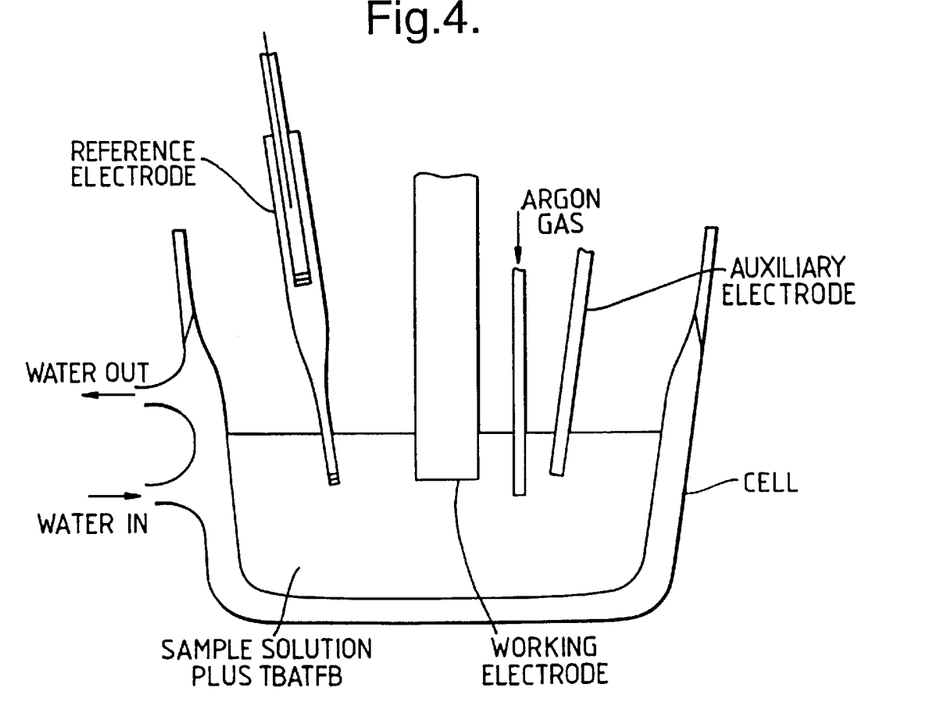
FIG. 4 shows a diagrammatic representation of a cyclic voltammetry apparatus as used to determine current flows in the measurements shown in FIG. 3.
Figure 5:
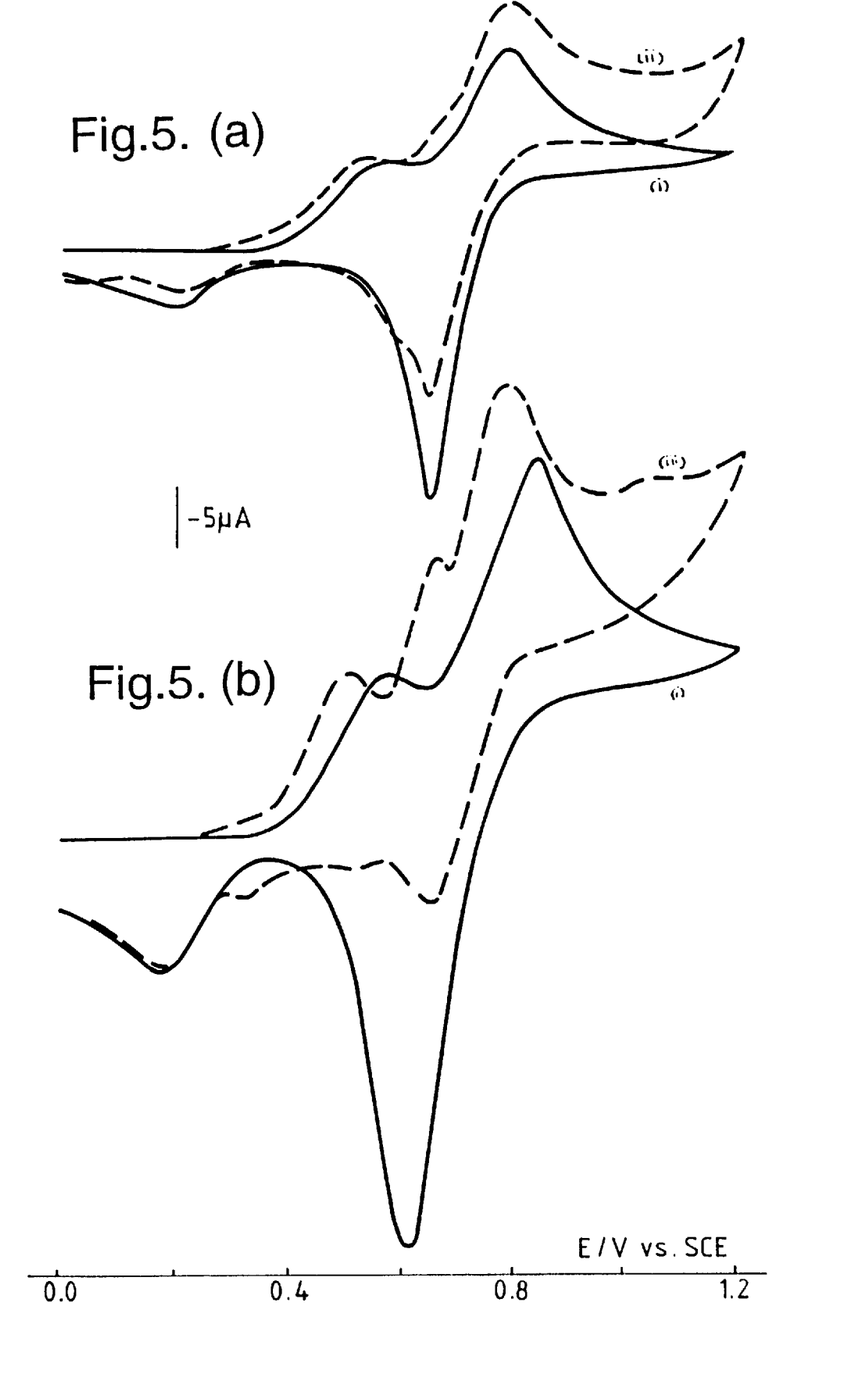

All electrochemical work was carried out on an EG & G PAR Potentiostat/Galvanostat Model 273. A platinum disc (ø 5 mm) or a glassy carbon disc (ø 7 mm) was used as working electrode, with a 1 cm$^2$ platinum gauss counter electrode. Reference electrodes were saturated calomel for $CH_2Cl_2$ and Ag+/Ag for $CH_3CN$. A one (see FIG. 4) or three compartment cell was used with solvents and supporting electrolyte being $CH_2Cl_2$ or $CH_3CN$ with $[CH_3(CH_2)_3]_4NBF_4$ respectively. A calix[4]arene of Formula I wherein $Y^1$ and $Y^4$ are groups (a) as set out in FIG. 1, $Y^2$ and $Y^3$ are hydrogen, $R^1$ and $R^4$ are methyl and $R^2$ and $R_3$ are hydrogen was subjected to cyclic voltammetry in a $CH_2Cl_2$ solution. Two redox current peak couples were produced using a scan rate of 50 mV/sec, both broader than that of a one electron transfer reaction (reversible or irreversible). While the redox behaviour of the calix[4]arene in solution alone ($3.7 \times 10^{-6}$M) can be attributed to the four ferrocenoyl groups, it suggests that these are subdivided into two subgroups on oxidation. Two of the four groups lose their electrons at lower potentials than the other two, and it is believed that this difference may be caused by the interaction between the two positively charged ferrocenoyl groups connected to the same nitrogen. The broadness of each peak can be attributed to the much weaker interaction between the two ferrocenoyl groups connected to the different nitrogen atoms ie. in the same subgroup, while the flexibility of these ferrocenoyl groups in solution may also contribute to peak broadness (see FIG. 5).

When the same solutions have neutral guests DMSO, DMS or DES added two changes are observed in the CV; (a) a shift of relative position of of each peak couple and (b) the splitting of the peak from a broad peak to two distinguishable peaks. This splitting effect is most pronounced with DMSO.

EXAMPLE 3

Effect of Guest Host Interaction on CV of a Solution of Calix[4]arenes in Method of the Invention.

Figure 1:
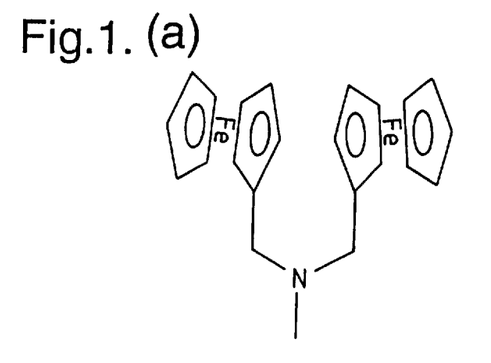

A calix[4]arene of Formula I wherein $Y^1$ and $Y^4$ are (b) as set out in FIG. 1, $Y^2$ and $Y^3$ are hydrogen, $R^1$ and $R^4$ are methyl and $R^2$ and $R^3$ are hydrogen was subjected to cyclic voltammetry in $CH_2Cl_2$ solution at $10^{-4}$M concentration. Two irreversible reduction peaks were observed.

Figure 6:
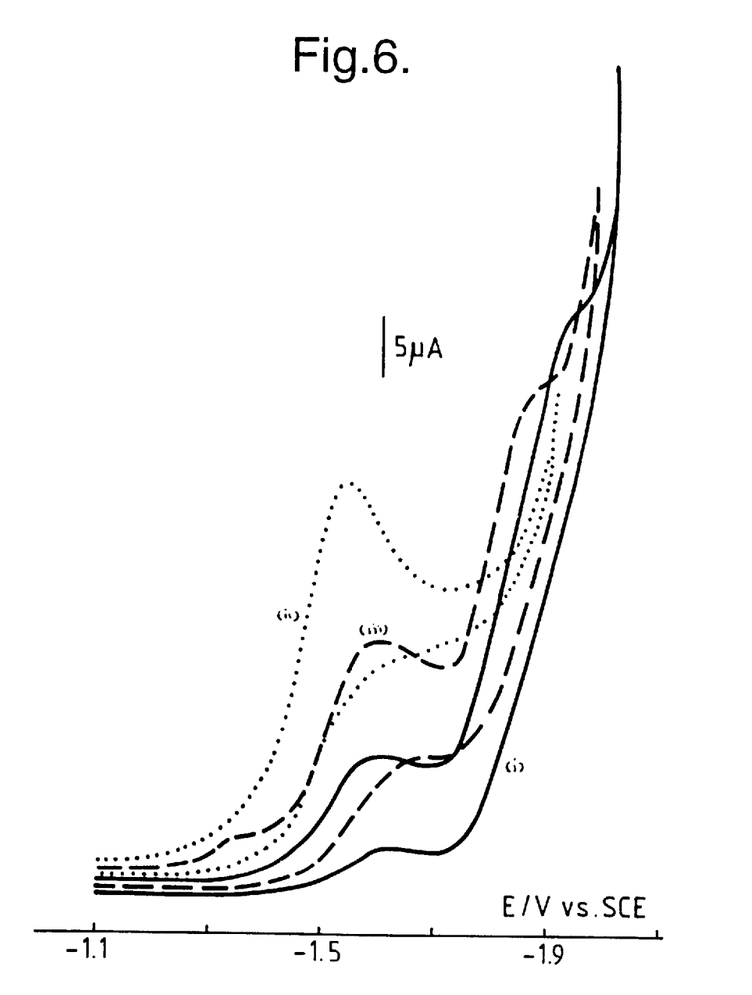
FIG. 6 shows cyclic voltammograms for (i) and calix[4] arene used in Example 3 below in $CH_2Cl_2$ solution, (ii) that solution with added DES and (iii) with added HMG.

The effect of DES and HMG is more obvious than for the calix[4]arene of Example 2, with the most significant change being that the current of the first peak increases with their concentration while the second decreases. For DES this change ends up with a merger of the two peaks and the appearance of a new current shoulder on the leftside of the first reduction peak with increasing concentration of HMG. Using this characteristic it is possible to identify HMG as related to DES in solution. Unlike the peak splitting effect of the calix[4]arene in Example 2, the current variation with the concentration of HMG and DES provides increased characterising information (see FIG. 6).

EXAMPLE 4

Effect of Guest Host Interaction on $^1$H NMR of Calix[4]arenes in the Method of the Invention Both calix[4]arenes of Examples 2 and 3 were studies by $^1$H NMR titration in the absence of the supporting electrolyte used therein. Changes in NMR spectra caused by adding DMSO, DMS, DES and HMG were observed, although less pronounced than in the CVs. Strongest changes were provided when DMSO was added to a $CH_2Cl_2$ solution of the compound of Example 2 whereupon the chemical shift range of the aromatic peaks was altered. For the addition of 1 to 5 equivalents of DMSO, 5 to 12 Hz (0.016 to 0.040 ppm) change resulted.

EXAMPLE 5

Synthesis of Calix[4]arenes having Pyrrole and Thiophene Containing Groups on the Lower Rim.

Figure 2:
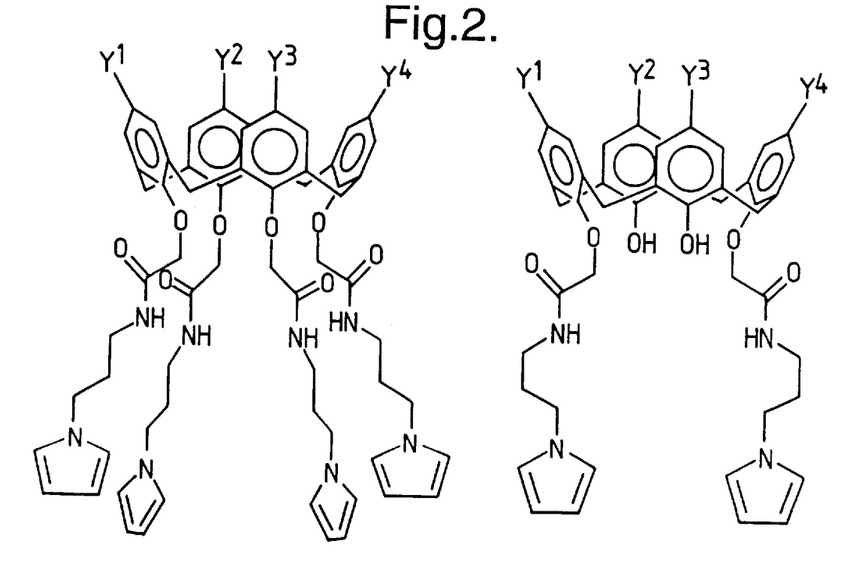
FIG. 2 shows the structure of two calix[4]arenes having lower rim groups $R^1$ to $R^4$ including polymerisable pyrrole moieties.
Figure 3:
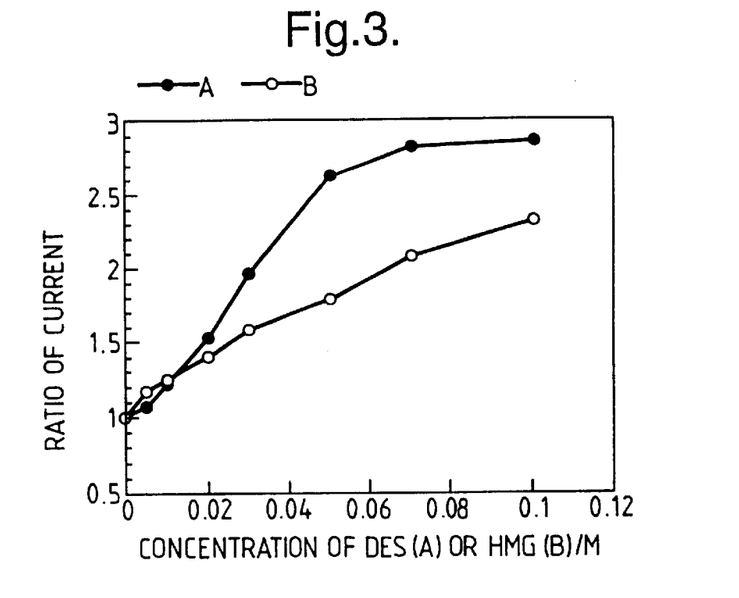
FIG. 3 shows a plot of the ratio of current against concentration of chemical agent for using a concentration of $10^{-4}M$ of calix[4]arene of Formula 1 wherein $R^1$ and $R^4$ are H, $R^2$ and $R^3$ are methyl, $Y^1$ and $Y^4$ are groups as set out in FIG. 1 (*b*) and $Y^2$ and $Y^3$ are H.

(a) Pyrrole groups: Calixarenes of desired upper rim substitution pattern for the intended end product have a desired number of their lower rim hydroxy groups converted to acid chloride groups by refluxing in excess thionyl chloride in dichloromethane. In the case of ferrocenyl end product a suitable precursor resistant to thionyl chloride is selected. The acid chloride is then reacted with a pyrrole amine in dichloromethane in the presence of pyridine; the pyrrole being preferably substituted in the N or 3 position with an alkyl chain on which the amine to be condensed is located. In the case of use of 3-pyrrole substitution the N hydrogen needs to be protected eg. with a posyl group. The alkylamino pyrrole group used in preparation of the compounds of FIG. 2 is commercially available.

(b) Thiophene groups: Calixarenes of desired upper rim substitution and having alkyl chains with a distal leaving group X on the lower rim is reacted with thiophene alcohol in the presence of base, yielding a thiophene substituted calixarene. The thiophene is substituted in the 3 position and the alkyl chain linking the hydroxy group to the pyrrole may be of any length.

Both these procedures may be applied to either thiophene or pyrrole groups, the thiophene amine replacing the pyrrole amine in the case of (a) and a pyrrole alocohol replacing thiophene alcohol in (b). In both cases the groups at the upper rim are selected according to their resilience to treatments (a) and (b).

EXAMPLE 6

Immobilisation of calix[4]arenes onto electrically conductive substrate surfaces; creation of calixarene host/guest interaction sensitive electrodes.

Calixarenes were copolymerised onto the surface of electrodes by consecutive potential cycling of an acetonitrile solution containing a mixture of $5 \times 10^{-4}$M of pyrrole and the calix[4]arene wherein $Y^1$ to $Y^4$ are each tertiary butyl and $R^1$ to $R^4$, as shown in Formula I, are as set out in Formula II of FIG. 2.

Attempts to form a conducting film from the calixarene of Formula II alone in acetonitrile failed, probably due to steric problems preventing chains having more than two pyrroles forming. Cyclic voltammograms from consecutive cycling of a $5 \times 10^{-3}$ M acetonitrile solution of just the calix[4]arene show an irreversible oxidation current wave, with current dropping dramatically during following scans. This indicates that the working electrode has been covered by an oxidised product which is insulating. Since the pyrroles are the only oxidisable groups the oxidation wave must relate to them, thus the coating must be a dimer, trimer or other oligomer of the calix[4]arene in which conjugation of pyrrole is not long enough to produce conductivity.

By forming the copolymer of the calix[4]arene with pyrrole longer chains of pyrrole moieties should be produced, thus allowing conductivity, and this is borne out by results of studies on the cyclic voltammetry of the two monomer acetonitrile solution, as compared to those on a $5 \times 10^{-4}$M pure pyrrole solution.

Two major differences can be seen; (a) the current increases such faster after each scan of the monomer mixture than the pure pyrrole and (b) the anodic branch of the redox wave couple, located before the sharp current increase due to oxidation of monomeric species is a single current peak for pure pyrrole but a current plateau for mixture. Since the redox couple corresponds to the oxidation and reduction of the polymer film itself the difference implies either the sense of the existence of the calixarene moieties connected to the polymer chain by the pyrrole units or the existence of two types of redox couple, calixarene affected and calixarene unaffected pyrrole units, in the polymer film.

The polymer coated electrodes derived from the CV of the acetonitrile solution were transfered to fresh background solutions of acetonitrile containing only 0.1M [$CH_3(CH_2)_3$]$_4NBF_4$ where both polymer films gave a linear increase with increasing potential scan rate; a characteristic of surface restrained redox species.

EXAMPLE 7

Electrochemical Studies on Further Calix[4]arenes

The electrochemical properties of the redox-active calix[4]arene derivatives 43, 44, 45, 46 and 49 were studies by cyclic voltammetry and square wave voltammetry by recording in dichloromethane with $1\times10^{-3}$ mol. $dm^{-3}$ of the host and [$NBu_4$][$BF_4$] as the supporting electrolyte, values quoted are relative to a Ag/Ag$^+$ reference electrode. Compounds 43, 44 and 45 all showed similar anodic and cathodic waves for the reversible oxidation of the ferrocene, a second, quasi-reversible wave appears at lower potential and is assumed to be due to the oxidation of the amine group.

The presence of a single wave due to the ferrocene oxidation in compounds 44 and 45 suggests that all the ferrocenes in these molecules are oxidised in two and four one electron processes respectively at around the same potential. It is intended to carry out coulombic studies to verify this. Square wave voltammetry studies with compounds 43, 44 and 45 similarly showed the presence of two oxidation peaks, the second of these due to oxidation of ferrocene.

Compound 46 showed a reversible oxidation wave due to the oxidation of ferrocene and a second irreversible peak at a higher potential. Compound 49 gave a reversible oxidation wave due to the oxidation of ferrocene and a second more complex peak at higher potential. In both cases the second peak is thought to be due to either the oxidation of the amide group or that of the phenol. Square wave voltammetry indicated that the second oxidation peak observed for 49 may be due to the occurence of two separate oxidation processes.

Compounds 43, 44, 45, 46 and 49 were studied by cyclic and square wave voltammetry in dichloromethane solution at a concentration of mustard guest of 0.05 mol $dm^{-3}$. No significant changes were observed in the electrochemical behaviour of 43, 44, 45 and 46 under these conditions but compound 49 gave a complex electrochemical response with a peak at around 0.95V disappearing and a new peak appearing at around 0.40V.

The electrochemical behaviour of compounds 46 and 49 was also studied in solutions containing either 1,1'-bischloroethyl ether, hemi-mustard or diethyl sulphide. No significant changes were observed with any of these guest thus demonstrating the specificity for 49 for the target mustard agent 1,1'-bischloroethyl sulphide.

EXAMPLE 8

Preparation of Electrodes Containing Compound 49 in PVC Matrix

Films of 49 in a PVC matrix were applied from a dichloromethane and DMF solutions by placing 30 μl of the solution onto a solid substrate electrode surface and allowing the solvent to evaporate leaving a visible film. Only films prepared with dichloromethane were studied. Substrates studied included glassy carbon, indium-tin oxide and platinum. The observation of an oxidation peak due to ferrocene by cyclic voltammetry indicated that 49 had been immobilised in the film but after three cycles the ferrocene oxidation peak disappeared, indicating that such immobilisation method would only be suitable for disposable electrode use. It is thought that the ferrocinium ion of compound 49 is soluble in the electrolye solution or that 49 is electrochemically decomposed under the conditions used.

TABLE 1

TABLE OF COMPOUNDS

| No. | R$^1$ | R$^2$ | R$^3$ | R$^4$ | Y$^1$ | Y$^2$ | Y$^3$ | Y$^4$ |
|---|---|---|---|---|---|---|---|---|
| 1 | H | H | H | H | tButyl | tButyl | tButyl | tButyl |
| 2 | H | H | H | H | H | H | H | H |
| 3 | Me | H | H | Me | H | H | H | H |
| 4 | CH$_2$Cp$_2$Fe | H | H | CH$_2$Cp$_2$Fe | H | H | H | H |
| 5 | CH$_2$CO$_2$Et | H | H | CH$_2$CO$_2$Et | H | H | H | H |
| 6 | CH$_2$CO$_2$tBu | H | H | CH$_2$CO$_2$tBu | H | H | H | H |
| 7 | Ts | H | H | Ts | H | H | H | H |
| 8 | Allyl | H | H | Allyl | H | H | H | H |
| 9 | Me | H | H | Me | H | H | H | H |
| 10 | Me | H | Me | Me | H | H | H | H |
| 11 | Ts | H | Ts | Ts | H | H | H | H |
| 12 | Ts | Ts | Ts | Ts | H | H | H | H |
| 13 | Me | H | Bn | Me | H | H | H | H |
| 14 | Me | Bn | Bn | Me | H | H | H | H |
| 15 | Ts | H | Allyl | Ts | H | H | H | H |
| 16 | Z | Z | Z | Z | H | H | H | H |
| 17 | Bn | Bn | Bn | Bn | H | H | H | H |
| 18 | Me | Allyl | Allyl | Me | H | H | H | H |
| 19 | Me | H | H | Me | H | NO$_2$ | NO$_2$ | H |
| 20 | Me | H | H | Me | H | NO | NO | H |
| 21 | Bn | H | H | Bn | H | NO | NO | H |
| 22 | CH$_2$CO$_2$Et | H | H | CH$_2$CO$_2$Et | H | NO | NO | H |
| 23 | Ts | H | H | Ts | H | NO$_2$ | NO$_2$ | H |
| 24 | Allyl | H | H | Allyl | H | NO$_2$ | NO$_2$ | H |
| 25 | Me | H | Me | Me | H | NO$_2$ | H | H |
| 26 | Me | H | Me | Me | H | NO$_2$ | H | H |
| 27 | Ts | H | Ts | Ts | H | NO$_2$ | H | H |
| 28 | Me | H | Bn | Me | H | NO$_2$ | H | H |

TABLE 1-continued

TABLE OF COMPOUNDS

| No. | $R^1$ | $R^2$ | $R^3$ | $R^4$ | $Y^1$ | $Y^2$ | $Y^3$ | $Y^4$ |
|---|---|---|---|---|---|---|---|---|
| 29 | Ts | H | Allyl | Ts | H | $NO_2$ | H | H |
| 30 | Ts | H | Q | Ts | H | $NO_2$ | Q | H |
| 31 | Allyl | H | Q | Allyl | H | $NO_2$ | Q | H |
| 32 | Me | H | H | Me | H | Allyl | Allyl | H |
| 33 | Me | H | H | Me | H | Prop2ene | Prop2ene | H |
| 34 | Me | H | H | Me | H | $CO_2H$ | $CO_2H$ | H |
| 35 | H | H | H | H | H | Allyl | Allyl | H |
| 36 | H | H | H | H | NDMA | NDMA | NDMA | NDMA |
| 37 | Ts | H | H | Ts | NDMA | NDMA | NDMA | NDMA |
| 38 | Ts | Ts | Ts | Ts | NDMA | NDMA | NDMA | NDMA |
| 39 | Me | H | H | Me | H | $NH_2$ | $NH_2$ | H |
| 40 | Ts | H | H | Ts | H | $NH_2$ | $NH_2$ | H |
| 41 | Me | H | Me | Me | H | $NH_2$ | H | H |
| 42 | Ts | H | Ts | Ts | H | $NH_2$ | H | H |

Q = quinone derivative
NDMA = N,N-dibenzylmethylamine

We claim:

1. A method for the detection of an uncharged chemical agent present in a sample comprising the steps of
   (1) exposing a calixarene, having a cyclic array of phenolic methylene monomers and having one or more redox active substituents on its upper rim, to a solution or suspension of the sample,
   (2) measuring any change in electrical properties of the calixarene during or after exposure to the solution or suspension as compared to a reference condition, and
   (3) relating such change in electrical properties to the presence of said chemical agent.

2. A method as claimed in claim 1 wherein the calixarene exposed to the solution or suspension is a calix[4]arene of Formula I Formula I wherein at least one of $Y^1$ to $Y^4$ is a redox active substituent; each remaining $Y^1$ to $Y^4$ is independently selected from the group consisting of hydrogen, alkyl, alkenyl, aryl and aralkyl and $R^1$ to $R^4$ are independently selected from the group consisting of hydrogen, alkyl, alkenyl, aryl, aralkyl and a polymerizable moiety.

3. A method as claimed in claim 2 wherein the polymerizable moiety has a polymerizable moiety or group on its end distal to the phenolic methylene monomers.

4. A method as claimed in claim 3 wherein the moiety is —$CH_2CONH(CH_2)_n$—$NC_4H_4$ or —$CH_2CONH(CH_2)_n$—$SC_4H_4$, where n is greater than, or equal to, 0.

5. A method as claimed in claim 4 wherein n is 2 to 4.

6. A method as claimed in claim 2 wherein the polymerizable moiety or group includes or is pyrrole, or thiophene or an analogous 5, 6 or 7 membered ring capable of polymerization with similar rings to provide a conductive polymer.

7. A method as claimed in claim 2 wherein said redox active substituent or substituents are independently a bis-(ferrocenoyl) or metal centered imino dipyridyl and derivatives and complexes of these, or one of the groups as set out below -continued and each remaining $Y^1$ to $Y^4$ is hydrogen.

8. A method as claimed in claim 2 wherein the chemical agent is from an environmental sample.

9. A method as claimed in claim 8 wherein the chemical agent is a chemical warfare agent.

10. A method as claimed in claim 9 wherein the chemical agent is a mustard.

11. A method as claimed in claim 2 wherein the calix[4] arene is one of

12. A polymer comprising the copolymerization product of a calixarene and one or more monomers capable of polymerizing to give an electrically conductive polymer; said calixarene having one or more redox active substituents on its upper rim and having one or more polymerizable moieties pendant from its lower rim.

13. A polymer as claimed in claim 12 wherein the polymerizable moieties are pendant from one or more oxygen atoms of lower rim hydroxy substituents of the calixarenes.

14. A polymer as claimed in claim 13 wherein the calixarene, and one or more monomers capable of polymerizing to given an electrically conductive polymer, include a pyrrole, thiophene and/or an analogous 5, 6 and 7 membered ring.

15. A polymer as claimed in claim 14 wherein the calixarene monomer is a compound of formula (I)

Formula 1 wherein at least one of the groups $R^1$ to $R^4$ has polymerizable moieties that can copolymerize with the monomer or monomers of (a).

16. A polymer as claimed in claim 13 wherein the phenolic methylene monomer (a) include a calixarene moiety that has a guest host interaction induced change in electrical property that can be determined by monitoring an electrical property of its copolymer product with (b).

17. An electrically conductive substrate comprising a conductive material coated with a thin film of a polymer as claimed in claim 12.

18. An electrode comprising a substrate coated with the polymers of claim 17 and means for connecting said substrate to an electrical circuit.

19. A method of manufacturing an electrically conductive substrate comprising the step of electropolymerizing a calixarene and one or more monomers capable of polymerizing to give an electrically conductive polymer, from a solution of the monomers in an organic solvent, said calixarene having one or more redox active substituents on its upper rim and having one or more polymerizable moieties pendant from it lower rim.

20. A method as claimed in claim 19 including the further steps of:
   dissolving equimolar amounts of the calixarene and monomers capable of polymerizing to give an electrically conductive polymer in an organic solvent,
   exposing the surface of a material to be coated to this solution, and
   placing an electrical potential across the solution via the material and a further electrode also exposed to the solution.

21. A calixarene of the formula:

wherein one or more of $Y^1$ to $Y^4$ comprises a redox active group independently selected from the group consisting of bis-(ferrocenoyl) and metal centered imino-dipyridyl containing groups.

22. A calixarene as claimed in claim 21 wherein the redox active group is independently selected from the groups shown below:

23. A calixarene as claimed in claim 21 wherein the redox active group is a ferrocene amide group.

24. A calixarene as claimed in claim 21 comprising two calix[4]arene moieties linked to a single ferrocene group by amide bonds.

25. A calixarene as claimed in claim 21 comprising two calix[4]arene moieties linked to a single dipyridyl group by amide bonds.

26. A calixarene as claimed in claim 21 comprising two calix[4]arene moieties linked to a single dipyridyl group by imido bonds.

* * * * *